United States Patent
Trihaas et al.

(10) Patent No.: US 11,758,914 B2
(45) Date of Patent: Sep. 19, 2023

(54) METHOD OF PRODUCING STREPTOCOCCUS THERMOPHILUS MUTANT STRAINS

(71) Applicant: Chr. Hansen A/S, Hoersholm (DK)

(72) Inventors: Jeorgos Trihaas, Hoersholm (DK); Thomas Janzen, Hoersholm (DK); Patrick Derkx, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 45 days.

(21) Appl. No.: 18/145,411

(22) Filed: Dec. 22, 2022

(65) Prior Publication Data

US 2023/0118835 A1   Apr. 20, 2023

Related U.S. Application Data

(62) Division of application No. 16/615,904, filed as application No. PCT/EP2018/064325 on May 31, 2018, now Pat. No. 11,564,399.

(30) Foreign Application Priority Data

May 31, 2017   (EP) .................................. 17173637

(51) Int. Cl.
| | |
|---|---|
| *C12N 1/20* | (2006.01) |
| *A23C 9/123* | (2006.01) |
| *C12N 7/00* | (2006.01) |
| *C12N 15/01* | (2006.01) |
| *C12R 1/46* | (2006.01) |

(52) U.S. Cl.
CPC ............... *A23C 9/1238* (2013.01); *C12N 1/20* (2013.01); *C12N 1/205* (2021.05); *C12N 7/00* (2013.01); *C12N 15/01* (2013.01); *A23C 2220/202* (2013.01); *C12N 2795/00031* (2013.01); *C12R 2001/46* (2021.05)

(58) Field of Classification Search
None
See application file for complete search history.

(56) References Cited

U.S. PATENT DOCUMENTS

| | | |
|---|---|---|
| 8,409,844 B2 | 4/2013 | Janzen et al. |
| 8,865,238 B2 | 10/2014 | Janzen et al. |
| 9,060,524 B2 | 6/2015 | Janzen et al. |
| 9,416,351 B2 | 8/2016 | Janzen et al. |
| 9,562,221 B2 | 2/2017 | Janzen et al. |
| 2015/0322415 A1 | 11/2015 | Janzen et al. |
| 2016/0165910 A1 | 6/2016 | Horvath et al. |

FOREIGN PATENT DOCUMENTS

| | | |
|---|---|---|
| WO | 2007/095958 A1 | 8/2007 |
| WO | 2007/144770 A2 | 12/2007 |
| WO | 2008/040734 A1 | 4/2008 |
| WO | 2011/092300 A1 | 8/2011 |

OTHER PUBLICATIONS

Binetti et al.; "Spontaneous phage-resistant mutants of Streptococcus thermophilus: Isolation and technological characteristics"; International Dairy Journal, vol. 17, issue 4; Apr. 2007; pp. 343-349 (abstract only).
Viscardi, M. et al.; "Selection of bacteriophage-resistant mutants of Streptococcus thermophilus"; Journal of Microbiological Methods (Nov. 2003), 55(1); pp. 109-119 (abstract only).
Wu et al., "Genomic insights into high exopolysaccharide-producing dairy starter bacterium Streptococcus thermophilus ASCC 1275," Scientific Reports, Vol. 4: 4974, 8 pages (May 2014).

*Primary Examiner* — Jennifer E Graser
(74) *Attorney, Agent, or Firm* — Foley & Lardner LLP

(57) ABSTRACT

The present invention is directed to a method of producing a *Streptococcus thermophilus* strain comprising the steps of
  a) Providing a mother strain in the form of *Streptococcus thermophilus* DSM32502,
  b) Growing a culture of the mother strain in the presence of a bacteriophage, to which the mother strain is not resistant, to obtain a number of mutant strains, which are resistant to the said bacteriophage,
  c) Measuring the acidification time of the bacteriophage-resistant mutant strains and the mother strain in a milk base and selecting at least one mutant strain with a reduced acidification time as compared to the mother strain to obtain a fast-acidifying mutant strain.

10 Claims, No Drawings

METHOD OF PRODUCING STREPTOCOCCUS THERMOPHILUS MUTANT STRAINS

CROSS-REFERENCE TO RELATED APPLICATIONS

The present application is a division of U.S. Application No. 16/615,904, filed Nov. 22, 2019, which is the U.S. National Stage of International Application PCT/EP2018/064325, filed May 31, 2018, and claims priority to European Patent Application No. 17173637.4 filed May 31, 2017.

FIELD OF THE INVENTION

The present invention relates to a method of producing a mutant of a mother strain in the form of *Streptococcus thermophilus* DSM32502.

BACKGROUND OF THE INVENTION

The bacterium *Streptococcus thermophilus* is used as a main component of starter cultures for producing fermented milk products, such as yogurt. In most countries it is mandatory to use a starter culture comprising both a *Streptococcus thermophilus* and a *Lactobacillus delbrueckii* spp. *bulgaricus* strain in order for the product to be designated the term yogurt.

Wu Q et al., *Scientific Reports*, 4:4974, DOI: 10.1038/srep04974, discloses a dairy starter bacterium *Streptococcus thermophilus* ASCC 1275, which has a high texturizing capacity. The strain yields the highest known amount (approx. 1,000 mg/L) of exopolysaccharide (EPS) in milk among the species of *S. thermophilus*.

SUMMARY OF THE INVENTION

The object of the present invention is to provide improved mutant strains of *Streptococcus thermophilus* DSM32502.

The object of the invention is achieved with the present invention, which is directed to a method of producing a *Streptococcus thermophilus* strain comprising the steps of
  a) Providing a mother strain in the form of *Streptococcus thermophilus* DSM32502,
  b) Growing a culture of the mother strain in the presence of a bacteriophage, to which the mother strain is not resistant, to obtain a number of mutant strains, which are resistant to the said bacteriophage,
  c) Measuring the acidification time of the bacteriophage-resistant mutant strains and the mother strain in a milk base and selecting at least one mutant strain with a reduced acidification time as compared to the mother strain to obtain a fast-acidifying mutant strain.

In general, the present invention is based on the surprising novel finding that it is possible to obtain mutants with reduced acidification time (increased acidification rate) when treating a mother strain with bacteriophages in order to obtain bacteriophage resistant mutants.

The present invention is further based on the surprising finding that when the texturizing *Streptococcus thermophilus* DSM32502 strain is treated with bacteriophages to obtain bacteriophage-resistant mutant strains a high proportion of the mutant strains have an improved acidification rate (growth rate), while at the same time the texturizing capacity is at the same level or even improved. This is a surprising finding, because bacteriophage resistant mutants of a mother strain with increased acidification rate will usually have a reduced texturizing capacity, because the bacterium cell will use additional carbohydrate source and energy for growth, which means that there will be less carbohydrate source and energy available to synthesize texturizing compound exopolysaccharide (EPS). However, in contrast thereto, the bacteriophage-resistant mutant strains of the present invention surprisingly have an increased acidification rate in combination with texturizing capacity of the same level or even a higher level than the mother strain.

The present invention further relates to a mutant strain of a mother strain in the form of *Streptococcus thermophilus* DSM32502, wherein the mutant strain is resistant to bacteriophage CHPC1057 deposited as DSM23962.

DETAILED DISCLOSURE OF THE INVENTION

Mother Strain

The mother strain *Streptococcus thermophilus* DSM32502 is an isolate of *Streptococcus thermophilus* ASCC 1275.

Treatment of the Mother Strain With Bacteriophage - Step B) of Method

The growing of the mother strain in the presence of a bacteriophage may be carried out using any conventional method for such purpose. In a particular embodiment of the invention, the growing of the culture of the mother strain in the presence of a bacteriophage, to which the mother strain is not resistant, is carried out by mixing a liquid sample of a single colony culture of the mother strain with a liquid sample of a single colony culture of the bacteriophage, adding a top agar, plating the resulting mixed culture on a suitable medium and incubating the plates overnight at 37° C. in anaerobic conditions.

In a particular embodiment of the invention, the bacteriophage is selected from the group consisting of CHPC1008 deposited as DSM32517, CHPC1057 deposited as DSM23962, and mixtures thereof. In a particular embodiment of the invention, the bacteriophage is CHPC1057 deposited as DSM23962.

In a particular embodiment of the invention, the single colony culture of the mother strain has been grown in a M17 medium containing 2 % lactose.

In a particular embodiment of the invention, the mixed culture is grown on a M17 medium containing 2 % lactose and 10 mM Ca/Mg.

In connection with the present invention the term "resistant to bacteriophage" means resistant in a standard double layer plague assay, where the reduction of the plaque number of 5 logarithms is considered to be phage resistant.

Measurement of Acidification Time - Step C) of Method

The measurement of the acidification time in a milk base may be carried out using any conventional method for measuring the acidification time of bacterium strains in a milk base. One such conventional method is measurement of acidification curves by a Cinac system (by Alliance Instruments, an AMS Company Brand). In a particular embodiment of the method of the invention, the acidification time is measured by change in a color indicator, e.g. Bromocresol Purple / Green in a 50/50 mixture In a particular embodiment of the invention, in step c) the mutant strain selected as compared to the mother strain has a acidification time of less than 99 %, preferably less than 98 %, more preferably less than 97 %, more preferably less than 96 %, more preferably less than 95 %, more preferably less than 94 %, more preferably less than 93 %, more preferably less than 92 %, more preferably less than 91 %, and most preferably less than 90 %.

In a particular embodiment of the method of the invention, in step c) the bacteriophage-resistant mutant strains and the mother strain are grown as single cultures.

In a particular embodiment of the method of the invention, in step c) the bacteriophage-resistant mutant strains and the mother strain are grown as a mixed culture, which in addition to the bacteriophage-resistant mutant strain or the mother strain contains at least one *Lactobacillus delbrueckii* spp. *bulgaricus* strain. In particular, the mixture culture in addition to the bacteriophage-resistant mutant strain or the mother strain contains at least one *Lactobacillus delbrueckii* spp. bulgaricus strain and at least one additional *Streptococcus thermophilus* strain.

Milk Base

The milk base used in step c) of the method of the invention may be any milk base, which is fermentable by a Streptococcus thermophilus strain. In a particular embodiment, the milk base is B-milk, wherein B-milk is re-constituted milk with a dry matter content of 9.5 %, which has been heat treated to 99° C. for 30 minutes in a batch process.

Measurement of Texturizing Capacity - Step D) of Method

In a particular embodiment of the invention, the method comprises the following additional step:

d) Measuring the texturizing capacity of the mutant strains selected in step c) and the mother strain in a milk base and selecting at least one mutant, which as compared to the mother strain has a texturizing capacity of least 90 % to obtain a fast-acidifying, texturizing mutant strain.

In a particular embodiment of the invention, in step d) the mutant strain selected as compared to the mother strain has a texturizing capacity of least 95 %, preferably at least 96 %, more preferably at least 97 %, more preferably at least 98 %, more preferably at least 99 %, more preferably at least 100 %, more preferably at least 101 %, more preferably at least 102 %, more preferably at least 103 %, more preferably at least 104 %, and most preferably at least 105 %.

In connection with the present invention the term "texturizing capacity" means shear stress as measured by the following method:

The day after incubation, the fermented milk product was brought to 13° C. and manually stirred gently by means of a stick fitted with a perforated disc until homogeneity of the sample. The rheological properties of the sample were assessed on a rheometer (Anton Paar Physica Rheometer with ASC, Automatic Sample Changer, Anton Paar® GmbH, Austria) by using a bob-cup. The rheometer was set to a constant temperature of 13° C. during the time of measurement. Settings were as follows:

Holding time (to rebuild to somewhat original structure) 5 minutes without any physical stress (oscillation or rotation) applied to the sample.

Oscillation step (to measure the elastic and viscous modulus, G' and G", respectively, therefore calculating the complex modulus G*)

Constant strain = 0.3 %, frequency (f) = [0.5..0.8] Hz 6 measuring points over 60 s (one every 10 s)

Rotation step (to measure shear stress at 300 1/s)

Two steps were designed:

1) Shear rate = [0.3-300] 1/s and 2) Shear rate = [275-0.3] 1/s. Each step contained 21 measuring points over 210 s (on every 10 s). The shear stress at 300 1/s was chosen for further analysis, as this correlates to mouth thickness when swallowing a fermented milk product.

Mutant Strain of the Invention

The present invention further relates to a *Streptococcus thermophilus* strain, which is a mutant of the *Streptococcus thermophilus* strain deposited as DSM32502, wherein the mutant strain carries a mutation, which renders the strain resistant to the bacteriophage CHPC1057 deposited as DSM23962.

In a particular embodiment of the invention, the mutant strain further carries a mutation, which renders the strain resistant to bacteriophage CHPC1008 deposited as DSM32517.

In a particular embodiment of the invention, the mutant strain has a reduced acidification time as compared to the *Streptococcus thermophilus* strain deposited as DSM32502. In particular, the mutant strain as compared to the *Streptococcus thermophilus* strain deposited as DSM32502 has a acidification time of less than 99 %, preferably less than 98 %, more preferably less than 97 %, more preferably less than 96 %, more preferably less than 95 %, more preferably less than 94 %, more preferably less than 93 %, more preferably less than 92 %, more preferably less than 91 %, and most preferably less than 90 %.

In a particular embodiment of the invention, the mutant strain as compared to the *Streptococcus thermophilus* strain deposited as DSM32502 has a texturizing capacity of least 95 %, preferably at least 96 %, more preferably at least 97 %, more preferably at least 98 %, more preferably at least 99 %, more preferably at least 100 %, more preferably at least 101 %, more preferably at least 102 %, more preferably at least 103 %, more preferably at least 104 %, and most preferably at least 105 %.

The present invention further relates to a *Streptococcus thermophilus* mutant strain selected from the group consisting of the *Streptococcus thermophilus* strain deposited as DSM32503, the *Streptococcus thermophilus* strain deposited as DSM32504, the *Streptococcus thermophilus* strain deposited as DSM32505, the *Streptococcus thermophilus* strain deposited as DSM32506, and the *Streptococcus thermophilus* strain deposited as DSM32507.

The present invention further relates to a *Streptococcus thermophilus* mutant strain obtainable by the method of the present invention.

In connection with the present invention, the term "mutant strain" means a strain obtained by the method of the invention. In particular, the term "mutant strain" means a strain obtained by the method of the invention and not subjected to any other mutagenization treatment. In particular, the term "mutant strain" means a strain obtained by at most 5 rounds, preferably at most 4 rounds, preferably at most 3 rounds, preferably at most 2 rounds, preferably 1 round of the method of the invention and not subjected to any other mutagenization treatment.

In a second aspect of the invention, the mutant strain as compared to the *Streptococcus thermophilus* strain deposited as DSM32502 has an increased texturizing capacity. In particular, the mutant strain as compared to the *Streptococcus thermophilus* strain deposited as DSM32502 has a texturizing capacity of at least 101 %, preferably at least 102 %, more preferably at least 103 %, more preferably at least 104 %, more preferably at least 105 %, more preferably at least 106 %, more preferably at least 107 %, more preferably at least 108 %, more preferably at least 109 %, and most preferably at least 110 %.

The second aspect of the invention is based on the surprising finding that a large proportion of mutants of a mother strain in the form of *Streptococcus thermophilus* DSM32502, wherein the mutant strain is resistant to bacteriophage CHPC1057 deposited as DSM23962, have an increased texturizing capacity.

In a particular embodiment of the second aspect of the invention, the mutant as compared to the *Streptococcus thermophilus* strain deposited as DSM32502 has a reduced acidification time. In particular, the mutant strain as compared to the *Streptococcus thermophilus* strain deposited as DSM32502 has an acidification time of less than 99 %, preferably less than 98 %, more preferably less than 97 %, more preferably less than 96 %, more preferably less than 95 %, more preferably less than 94 %, more preferably less than 93 %, more preferably less than 92 %, more preferably less than 91 %, and most preferably less than 90 %. In another particular embodiment of the second aspect of the invention, the mutant as compared to the *Streptococcus thermophilus* strain deposited as DSM32502 has an acidification time, which as compared to the *Streptococcus thermophilus* strain deposited as DSM32502 is equal or higher.

Method of Producing a Fermented Milk Product

The present invention further relates to a method of producing a fermented milk product comprising using a starter culture comprising the mutant strain of the invention or the mutant strain obtained in the method of the invention.

Starter Culture

The starter culture used in the process of the invention may be any starter culture comprising a *Streptococcus thermophilus* strain.

In the present context, a yogurt starter culture is a bacterial culture which comprises at least one *Lactobacillus delbrueckii* subsp *bulgaricus* strain and at least one *Streptococcus thermophilus* strain. In accordance herewith, the term "yogurt" refers to a fermented milk product obtainable by inoculating and fermenting milk with a composition comprising a *Lactobacillus delbrueckii* subsp *bulgaricus* strain and a *Streptococcus thermophilus* strain.

Most conventional starter cultures used for producing various types of fermented milk products are suitable for use in the process of the invention. Preferred starter cultures are those, which produce fermented milk products with high texture and/or texture. Also, it is preferred that the fermented milk product produced is resistant to subsequent heat treatment.

In a preferred embodiment of the invention, the starter culture comprises one or more Lactic Acid Bacteria (LAB) strains selected from the group consisting of lactic acid bacteria strains from the order "Lactobacillales". Preferably, the starter culture comprises one or more Lactic Acid Bacteria (LAB) strains selected from the group consisting of *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp.

In a preferred embodiment of the invention, the starter culture in a fermentation of a milk substrate, which contains 3.0 % protein, 2.8 % fat and 1.5 % modified starch, is capable of generating a starter culture fermented milk product with a shear stress measured at 300 1/s of above 50 Pa, preferably above 60 Pa, more preferably above 70 Pa, and most preferably above 80 Pa.

In the process of the invention, it is preferred that the starter culture has an acidification capacity so that the fermented milk product reaches a pH of 4.3 in less than 12 hours, preferably less than 10 hours, more preferably less than 9 hours, more preferably less than 8 hours, and most preferably less than 7 hours.

In the process of the invention, it is preferred that the starter culture has a low level of post-acidification at the target pH. In a preferred embodiment of the invention, the starter culture in a fermentation of a milk substrate, which contains 3.0 % protein, after reaching a target pH of 4.3 generates a post-acidification of below 0.30 pH units in 24 hours, preferably below 0.25 pH units in 24 hours, more preferably below 0.20 pH units in 24 hours, more preferably below 0.15 pH units in 24 hours, more preferably below 0.10 pH units in 24 hours, and most preferably below 0.05 pH units in 24 hours.

Milk Substrate

The term "milk" is to be understood as the lacteal secretion obtained by milking any mammal, such as a cow, a sheep, a goat, a buffalo or a camel. In a preferred embodiment, the milk is cow's milk. The term milk also includes protein/fat solutions made of plant materials, e.g. soy milk and grain milk, including oat milk and wheat milk.

The term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder.

Preferably, at least part of the protein in the milk substrate is proteins naturally occurring in milk, such as casein or whey protein. However, part of the protein may be proteins which are not naturally occurring in milk.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

In a particular embodiment of the invention, the milk substrate used in the process of the invention contains a texturizing agent, such as a thickener and a stabilizer. Preferably, the texturizing agent is selected from the group consisting of starch, modified starch, gellan gum, pectin, alginate, agar agar, guar gum, Locust Bean Gum (LBG, carob gum), carrageenan, gelatin and Whey Proteins, e.g. Whey Protein Concentrate (WPC). Such milk substrates are typically used for producing Post Pasteurized Yogurt (PPY).

In a preferred embodiment of the invention, the milk substrate used for the fermentation with the starter culture contains a sugar-containing composition. Preferably, the sugar-containing composition is selected from the group consisting of an artificial sugar; a High Intensity Natural Sweetener; and a sugar syrup, a puree, a juice and a nectar obtained from a source selected from the group consisting of a fruit, a vegetable and a grain. Preferably, the sugar syrup is selected from the group consisting of maple syrup, a corn syrup, a glucose syrup, a high-fructose corn syrup and golden syrup.

In connection with the present invention the term "sugar" means a natural saccharide selected from the group consisting of fructose, glucose, sucrose and mixtures thereof, an artificial sugar or a High Intensity Natural Sweetener.

Preferably, the High Intensity Natural Sweetener is a steviol glycoside, incl. stevia. Preferably, the artificial sugar is a High Intensity Artificial Sweetener selected from the group consisting aspartame, sucralose, neotame, acesulfame potassium, saccharin, advantame and cyclamates.

In a preferred embodiment of the invention, the milk substrate used for the fermentation with the starter culture has a protein content of between 1 % by weight (w/w) and 8.0 % by weight (w/w), preferably between 1.2 % by weight (w/w) and 7.0 % by weight (w/w), more preferably between 1.4 % by weight (w/w) and 6.0 % by weight (w/w) preferably between 1.6 % by weight (w/w) and 5.0 % by weight (w/w), preferably between 1.8 % by weight (w/w) and 4.5 % by weight (w/w), and most preferably between 2.0 % by weight (w/w) and 4.0 % by weight (w/w).

In a preferred embodiment of the invention, the milk substrate used for the fermentation with the starter culture has a fat content of between 1 % by weight (w/w) and 8.0 % by weight (w/w), preferably between 1.2 % by weight (w/w) and 7.0 % by weight (w/w), more preferably between 1.4 % by weight (w/w) and 6.0 % by weight (w/w) preferably between 1.6 % by weight (w/w) and 5.0 % by weight (w/w), preferably between 1.8 % by weight (w/w) and 4.5 % by weight (w/w), and most preferably between 2.0 % by weight (w/w) and 4.0 % by weight (w/w).

In a preferred embodiment of the invention, the milk substrate used for the fermentation with the starter culture contains an additive selected from the group consisting of a grain; and a puree, a juice and a nectar obtained from a source selected from the group consisting of a fruit, a vegetable and a grain. The grain may e.g. be in the form of a grain flour.

Fermentation

"Fermentation" in the methods of the present invention means the conversion of carbohydrates into alcohols or acids through the metabolism of a microorganism. Preferably, fermentation in the methods of the invention comprises conversion of lactose to lactic acid.

Fermentation processes to be used in production of fermented milk products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a dairy product in solid or liquid form (fermented milk product).

In a preferred embodiment of the process of the invention the target pH is from 3.80 to 4.39, preferably from 3.80 to 4.38, more preferably from 3.80 to 4.37, more preferably from 3.80 to 4.36, more preferably from 3.80 to 4.35, more preferably from 3.80 to 4.34, more preferably from 3.80 to 4.33, more preferably from 3.80 to 4.32, more preferably from 3.80 to 4.31, more preferably from 3.80 to 4.30, more preferably from 3.90 to 4.30, and most preferably from 4.00 to 4.30.

In general it is preferred that fermented milk products have a pH of below 3.90 for reasons of food safety, in particular to prevent growth of pathogenic microorganisms. On the other hand it is preferred that fermented milk products have a pH of above 4.00 for reasons of flavor and taste.

Fermented Milk Product

The present invention further relates to a fermented milk product containing the mutant strain of the invention or the mutant strain obtained in the method of the invention.

The fermented milk product of the invention may be any fermented milk product, which can be produced using a starter culture comprising a *Streptococcus thermophilus* strain.

The term "fermented milk product" as used herein refers to a food or feed product wherein the preparation of the food or feed product involves fermentation of a milk substrate with a lactic acid bacteria. "Fermented milk product" as used herein includes but is not limited to products such as thermophilic fermented milk products, e.g. yoghurt, mesophilic fermented milk products, e.g. sour cream and buttermilk, as well as fermented whey.

The term "thermophile" herein refers to microorganisms that thrive best at temperatures above 35° C. The industrially most useful thermophilic bacteria include *Streptococcus* spp. and *Lactobacillus* spp. The term "thermophilic fermentation" herein refers to fermentation at a temperature above about 35° C., such as between about 35° C. to about 45° C. The term "thermophilic fermented milk product" refers to fermented milk products prepared by thermophilic fermentation of a thermophilic starter culture and include such fermented milk products as set-yoghurt, stirred-yoghurt and drinking yoghurt, e.g. Yakult.

The term "mesophile" herein refers to microorganisms that thrive best at moderate temperatures (15° C.-35° C.). The industrially most useful mesophilic bacteria include *Lactococcus* spp. and *Leuconostoc* spp. The term "mesophilic fermentation" herein refers to fermentation at a temperature between about 22° C. and about 35° C. The term "mesophilic fermented milk product" refers to fermented milk products prepared by mesophilic fermentation of a mesophilic starter culture and include such fermented milk products as buttermilk, sour milk, cultured milk, smetana, sour cream, Kefir and fresh cheese, such as quark, tvarog and cream cheese.

In a particular embodiment of the invention, the fermented milk product is selected from the group consisting of set yogurt, stirred yogurt, buttermilk, sour milk, cultured milk, Smetana, sour cream, Kefir, fresh cheese and quark.

Examples of cheeses which are prepared by fermentation with *Streptococcus thermophilus* and *Lactobacillus delbrueckii* subsp. *bulgaricus* include Mozzarella and pizza cheese (Høier et al. (2010) in *The Technology of Cheesemaking*, 2nd Ed. Blackwell Publishing, Oxford; 166-192).

Preferably, the fermented milk product is a yogurt.

In a preferred embodiment the concentration of *Streptococcus thermophilus* cells inoculated is from $10^4$ to $10^9$ CFU *Streptococcus thermophilus* cells per ml of milk substrate, such as from $10^4$ CFU to $10^8$ CFU *Streptococcus thermophilus* cells per ml of milk substrate.

DEFINITIONS

In connection with the present invention the terms and expressions listed below have the following meaning:

The expression "acidification time" means the period of time from the start of the fermentation to the target pH has been reached. The expression "the mutant strain as compared to the mother strain has an acidification time of less than XX %," is to be calculated as the percentage of the acidification time of the mutant strain to the acidification time of the mother strain.

The expression "acidification rate" means the speed of acidification, i.e. the change in pH unit per unit of time.

The expression "lactic acid bacteria" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "*Lactobacillales*" which includes *Lactococcus spp.*, *Streptococcus spp.*, *Lactobacillus spp.*, *Leuconostoc spp.*, *Pseudoleuconostoc* spp., *Pediococcus spp.*, *Brevibacterium spp.*, *Enterococcus spp.* and *Propionibacterium spp.* These are frequently used as food cultures alone or in combination with other lactic acid bacteria.

Lactic acid bacteria, including bacteria of the species *Lactobacillus* sp. and *Lactococcus* sp., are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product or a cheese. Such lactic acid bacterial cultures are in general referred to as "starter cultures" or "starters".

In the present context the term "fruit juice" refers to the liquid naturally contained in fruit prepared by mechanically squeezing or macerating fresh fruits without the presence of heat and solvents. The "fruit juice" may consist of juice from one type of fruit or a mixture of more than one type of fruit. The "fruit juice" may be either one containing pulp, or one from which the pulp has been removed by such an operation as centrifugation.

The term "nectar" in the present context refers to a beverage having a fruit juice content of between 30 to 99% fruit juice.

In the present context the term "puree" refers to fruits prepared by grounding, pressing and/or straining into the consistency of a thick liquid or a soft paste without the presence of heat and solvents. "Puree" is made of 100% fruit as opposed to being made from just the juice of the fruit.

The term "target pH" means the pH at which the fermentation is deemed to be finished, and from the point in time at which the target pH is reached the starter culture fermented milk product is ready for further processing, e.g. heat treatment.

The term "grain" means any product obtained from a cereal or grain biological source material, including oat, corn, barley, rye, buckwheat, wheat and rice.

The expression "X.Xx10expYY" and "X.XEYY", both mean $X.Xx10^{YY}$, and the two said expressions are used interchangeably.

The expression "CFU" means Colony Forming Units.

ITEMS OF THE INVENTION

1. A method of producing a *Streptococcus thermophilus* strain comprising the steps of
    a) Providing a mother strain in the form of *Streptococcus thermophilus* DSM32502,
    b) Growing a culture of the mother strain in the presence of a bacteriophage, to which the mother strain is not resistant, to obtain a number of mutant strains, which are resistant to the said bacteriophage,
    c) Measuring the acidification time of the bacteriophage-resistant mutant strains and the mother strain in a milk base and selecting at least one mutant strain with a reduced acidification time as compared to the mother strain to obtain a fast-acidifying mutant strain.
2. A method according to item 1, wherein the bacteriophage is selected from the group consisting of CHPC1008, CHPC1057 and mixtures thereof.
3. A method according to any of items 1-2, wherein in step c) the mutant strain selected as compared to the mother strain has a acidification time of less than 99 %, preferably less than 98 %, more preferably less than 97 %, more preferably less than 96 %, more preferably less than 95 %, more preferably less than 94 %, more preferably less than 93 %, more preferably less than 92 %, more preferably less than 91 %, and most preferably less than 90 %.
4. A method according to any of items 1-3, wherein in step c) the bacteriophage-resistant mutant strains and the mother strain are grown as single cultures.
5. A method according to any of items 1-3, wherein in step c) the bacteriophage-resistant mutant strains and the mother strain are grown as a mixed culture, which in addition to the mutant strain or the mother strain contains at least one *Lactobacillus delbrueckii* spp. *bulgaricus* strain.
6. A method according to any of items 1-5 comprising the following additional step:
    d) Measuring the texturizing capacity of the mutant strains selected in step c) and the mother strain in a milk base and selecting at least one mutant strain, which as compared to the mother strain has a texturizing capacity of least 90 % to obtain a fast-acidifying, texturizing mutant strain.
7. A method of item 6, wherein in step d) the mutant strain selected as compared to the mother strain has a texturizing capacity of least 95 %, preferably at least 96 %, more preferably at least 97 %, more preferably at least 98 %, more preferably at least 99 %, more preferably at least 100 %, more preferably at least 101 %, more preferably at least 102 %, more preferably at least 103 %, more preferably at least 104 %, and most preferably at least 105 %.
8. A mutant strain of a mother strain in the form of *Streptococcus thermophilus* DSM32502, wherein the mutant strain is resistant to bacteriophage CHPC1057.
9. A mutant strain according to item 8, wherein the mutant strain is further resistant to bacteriophage CHPC1008.
10. A mutant strain according to item 8 or 9, wherein the mutant strain as compared to the mother strain has a acidification time of less than 99 %, preferably less than 98 %, more preferably less than 97 %, more preferably less than 96 %, more preferably less than 95 %, more preferably less than 94 %, more preferably less than 93 %, more preferably less than 92 %, more preferably less than 91 %, and most preferably less than 90 %.
11. A mutant strain according to any of items 8-10, wherein the mutant strain as compared to the mother strain has a texturizing capacity of least 95 %, preferably at least 96 %, more preferably at least 97 %, more preferably at least 98 %, more preferably at least 99 %, more preferably at least 100 %, more preferably at least 101 %, more preferably at least 102 %, more preferably at least 103 %, more preferably at least 104 %, and most preferably at least 105 %.

12. A *Streptococcus thermophilus* mutant strain selected from the group consisting of the *Streptococcus thermophilus* strain deposited as DSM32503, the *Streptococcus thermophilus* strain deposited as DSM32504, the *Streptococcus thermophilus* strain deposited as DSM32505, the *Streptococcus thermophilus* strain deposited as DSM32503, the *Streptococcus thermophilus* strain deposited as DSM32506, and the *Streptococcus thermophilus* strain deposited as DSM32507.

13. A method of producing a fermented milk product comprising using a starter culture comprising the mutant strain of any of items 8-12 or the mutant strain obtained in the method of any of items 1-7.

14. A fermented milk product containing the mutant strain of any of items 8-12 or the mutant strain obtained in the method of any of items 1-7.

15. A mutant strain of a mother strain in the form of *Streptococcus thermophilus* DSM32502, wherein the mutant strain is resistant to bacteriophage CHPC1057, and wherein the mutant as compared to the mother strain has an increased texturizing capacity.

EXAMPLES

Example 1: Bacteriophage Typing of Streptococcus Thermophilus CHCC23369

The sensitivity / resistance of *Streptococcus thermophilus* CHCC23369 (ASCC 1275) to a number of bacteriophages was tested using the following method:

Procedure for Colorimetric Microtiter Plate Assay for Bacteriophage Typing

Phage typing is performed in a microtiter plate based inhibition test.

The test phages are distributed in a microtiter plate containing sterilized 9.5% skim milk and a colorimetric pH indicator. Each phage is added to a final concentration of 1.0E06 phages/ml. A control is made containing the indicator milk without phage addition.

The test strain is inoculated 1% in the microtiter wells from an overnight culture. The acidification is followed by periodical scanning of the microtiter plates on a flatbed scanner and translation of the color values into pH values by specific software resulting in pH curves for the strain infected with each single phage and the strain without added phages.

The pH of the phage containing well and the control well is compared when the control well without a phage shows a pH of 5.0. For each single phage containing well the pH difference is measured at this control pH, and a sample is considered to be positive (phage sensitive) if the difference in pH is higher than 0.3 pH units.

Results

It was found that *Streptococcus thermophilus* CHCC23369 is resistant to a total of 41 tested bacteriophages, whereas the strain is sensitive to the bacteriophages CHPC1057 and CHPC1008.

Example 2: Producing Bacteriophage-Resistant Mutants of Streptococcus Thermophilus CHCC23369

Medium M17

The M17 agar medium has the following composition (g/l):
Tryptone: 2.5 g
Peptic digest of meat: 2.5 g
Papaic digest of soybean meal: 5.0 g
Yeast extract: 2.5 g
Meat extract: 5.0 g
Lactose: 5.0 g
Sodium-glycero-phosphate: 19.0 g
Magnesium sulphate, 7 H2O: 0.25 g
Ascorbic acid: 0.5 g
Agar: 15.0 g
Milli-Q water: 1000 ml.
pH is adjusted to final pH 7.1±0.2 (25° C.)

Plating Procedure

A single colony of *Streptococcus thermophilus* CHCC23369 was inoculated into 10 ml M17 - 2 % lactose medium in a tube. The tube was incubated overnight at 37° C. 2 x 1.5 ml including 15 % glycerol was frozen for stock at -40° C.

A sample of the bacteriophage CHPC1057 was sterile filtered with a 0.2 µm filter and $10^{-1}$ and $10^{-2}$ dilutions in ringer solution were prepared.

For each of dilutions $10^0$, $10^{-1}$ and $10^{-2}$, 5x100 µl of stock CHCC23369 was mixed with 5x100 µl CHPC1057 in tubes, top agar was added, and the tubes were incubated for 5 minutes at room temperature and plated on plates with a M17 - 2 % lactose + 10 mM Ca/Mg medium. The plates were incubated overnight at 37° C. at anaerobic conditions.

Colonies appeared on plates with $10^{-1}$ and $10^{-2}$ dilution. 20 colonies were selected for cross-streak against CHPC1057 and with CHCC23369 at the bottom of each plate, and the plates were incubated overnight at 37° C. at anaerobic conditions. 10 colonies with the putative bacteriophage-resistant mutants were selected for purification. The 10 mutants were purified 3 times by plating on plates with a M17 -2 % lactose + 10 mM Ca/Mg medium and incubation overnight at 37° C. at anaerobic conditions.

From single colonies each mutant were inoculated in tubes with 10 ml M17 - 2 % lactose and incubated overnight at 37° C. at anaerobic conditions. Each mutant was frozen with 15 % glycerol (1.5 ml in total) in ampoules.

Viscosity Test

All 10 mutants and the mother strain was inoculated from overnight cultures in bottles with 200 B-milk and incubated overnight at 37° C. The 11 bottles were taken from 37° C. and cooled to room temperature and a pipette viscosity test was made by measuring the efflux time of the fermented milk through a 25 ml pipette (3 repetitions).

TABLE 1

| Efflux time of mutants and mother strain | | | | | |
|---|---|---|---|---|---|
| Efflux time (seconds) | 1 | 2 | 3 | Average | pH |
| Mother strain | 46 | 45 | 45 | 45 | 4.33 |
| Mutant 1 | 44 | 38 | 37 | 40 | 4.20 |
| Mutant 2 | 45 | 45 | 41 | 44 | 4.29 |
| CHCC27510 | 51 | 53 | 50 | 51 | 4.31 |
| Mutant 5 | 47 | 44 | 45 | 45 | 4.31 |
| CHCC27511 | 48 | 51 | 44 | 48 | 4.33 |
| Mutant 8 | 49 | 47 | 44 | 47 | 4.33 |
| CHCC27512 | 52 | 53 | 44 | 50 | 4.34 |
| CHCC27806 | 46 | 43 | 40 | 43 | 4.34 |
| CHCC27513 | 53 | 51 | 49 | 44 | 4.33 |
| Mutant 17 | 42 | 46 | 43 | 44 | 4.27 |

Based on the viscosity test results 5 of the 10 mutants were selected for further testing with respect to texturizing capacity and acidification time and given the following numbers: CHCC27510, CHCC27511, CHCC27512, CHCC27513, and CHCC27806.

Phage resistance to CHPC1057 and CHPC1008 was confirmed.

Example 3: Acidification Time and Texturizing Capacity (Shear Stress) of 3 Bacteriophage-Resistant Mutants of *Streptococcus Thermophilus* CHCC23369

The mother strain CHCC23369 and the mutants CHCC27511, CHCC27512 and CHCC27513 were tested for their acidification time and texturizing capacity (shear stress).

Acidification / Fermentation

Milk Base: Semi fat milk (1.5 % fat and 2.0 % Skimmed Milk Powder (SMP))

All strains to be tested were inoculated (1 %) into bottles containing 200 ml milk base and the fermentation was carried out at 40° C. until a pH of 4.55 was reached.

Shear Stress

The shear stress was measured using the following method:

The day after incubation, the fermented milk product was brought to 13° C. and manually stirred gently by means of a stick fitted with a perforated disc until homogeneity of the sample. The rheological properties of the sample were assessed on a rheometer (Anton Paar Physica Rheometer with ASC, Automatic Sample Changer, Anton Paar® GmbH, Austria) by using a bob-cup. The rheometer was set to a constant temperature of 13° C. during the time of measurement. Settings were as follows:

Holding time (to rebuild to somewhat original structure) 5 minutes without any physical stress (oscillation or rotation) applied to the sample.

Oscillation step (to measure the elastic and viscous modulus, G' and G", respectively, therefore calculating the complex modulus G*)

Constant strain = 0.3 %, frequency (f) = [0.5..0.8] Hz 6 measuring points over 60 s (one every 10 s)

Rotation step (to measure shear stress at 300 1/s)

Two steps were designed:

1) Shear rate = [0.3-300] 1/s and 2) Shear rate = [275-0.3] 1/s. Each step contained 21 measuring points over 210 s (on every 10 s). The shear stress at 300 1/s was chosen for further analysis, as this correlates to mouth thickness when swallowing a fermented milk product.

Results

TABLE 2

| Acidification time and shear stress for 3 bacteriophage-resistant mutants and the mother strain | | | | |
|---|---|---|---|---|
| | Acidification time (time to pH 4.55) | Acidification time as compared to mother strain (%) | Shear stress (Pa) | Shear stress as compared to mother strain (%) |
| Mother strain CHCC23369 | 9.0 hours | 100.0 | 68.2 | 100.0 |
| Mutant CHCC27511 | 8.5 hours | 94.4 | 69.8 | 102.3 |
| Mutant CHCC27512 | 8.5 hours | 94.4 | 66.8 | 97.9 |
| Mutant CHCC27513 | 8.5 hours | 94.4 | 66.9 | 98.1 |

As will appear from Table 2, mutants CHCC27511, CHCC27512, CHCC27513 had a lower acidification time than the mother strain.

As will also appear from Table 2, mutant CHCC27511 had an increased shear stress as compared to the mother strain. Mutants CHCC27512 and CHCC27513 had a slightly decreased shear stress as compared to the mother strain.

Example 4: Acidification Time and Texturizing Capacity (TADM) of 3 Bacteriophage-Resistant Mutants of *Streptococcus Thermophilus* CHCC23369

The *Streptococcus thermophilus* (St) mutants CHCC27510, CHCC27512, and CHCC27806 were tested in a process for producing yogurt for their acidification time and texturizing capacity (viscosity and gel stiffness). The mutants were tested both as single culture and in combination with a commercial starter culture blend, wherein the mutant is replacing a texturizing *Streptococcus thermophilus* of the commercial starter culture. The results are compared with the aforementioned commercial starter culture blend and with the texturizing *Streptococcus thermophilus* of the commercial starter culture.

Milk Base

The milk base is a milk base suitable for producing Post Pasteurized Yogurt (PPY).

The milk base has the following composition:

TABLE 3

Composition of milk base

| Raw Materials/ Ingredients | Specifications | Dosage (%) |
|---|---|---|
| Fresh Milk 3.5% fat | Whole milk 3.5% fat | 74.3 |
| Sugar | Sugar | 7.0 |
| WPC 80 | Nutrilac YO-7830, Arla Food Ingredients | 0.6 |
| Modified starch | | 1.5 |
| LMA Pectin | Clearam CJ5025, Roquette | 0.12 |
| Gellan gum (High & Low Acyl Gellan Gum) | LM-106 AS-YA, CP Kelco Kelcogel YSS, CP Kelco | 0.03 |
| Water | Water | Add up to 100% |
| Total | Fat % - Calculated | 2.8% |
| | Protein % - Calculated | 3.0% |

Procedure for Preparing Milk Base and for Fermentation

1) Dry blend pectin, starch, milk powder and sugar. Add the dry blend to the milk using a high speed mixer or tri-blender for the three milk bases; Stir until the ingredients have been dispersed and allow the mix to fully hydrate (min. 2 hours)
2) Measure fat and protein level on Milko Scan
3) De-aeration at 350-400 mbar
4) Homogenize at 60° C. at 150 bar
5) Pasteurization at 95° C. for 5 minutes on the big plate heat exchanger (pasteurizer)
6) Cool to 5° C.

Starter Culture

The starter culture used was YoFlex YF-L904. It contains 3 Streptococcus thermophilus strains and 1 Lactobacillus delbrueckii subsp. bulgaricus strain.

Acidification / Fermentation

The fermentation was carried out in a microtiter plate using a robot. The acidification time to pH 4.4 was measured. The pH was measured by change in the color (hue) of a blue indicator.

Measurement of Texturizing Capacity

The texturizing capacity was measured in a Hamilton robot as dynamic viscosity as a measurement of TADM (Total Aspiration and Dispense Monitoring). Reference is made to WO2015086574 for a more detailed description of the method.

Results

Acidification Time

TABLE 4

Acidification time of 3 bacteriophage-resistant mutants of Streptococcus thermophilus CHCC23369

| | Acidification time (time to pH 4.4 (min)) | Acidification time as compared to mother strain (%) |
|---|---|---|
| Commercial texturizing strain | ND | |
| Mutant CHCC27510 | 1130 | ND |
| Mutant CHCC27512 | 1131 | ND |
| Mutant CHCC27806 | 1131 | ND |
| Commercial starter | 434 | 100.0 |
| Starter with CHCC27510 | 428 | 97.7 |
| Starter with CHCC27512 | 428 | 97.7 |
| Starter with CHCC27806 | 428 | 97.7 |

As will appear from Table 4, all of the mutants had a reduced acidification time as compared to the commercial texturizing strain, when grown as a starter culture blend.

Texturizing Capacity

TABLE 5

TADM values for viscosity and gel stiffness of 3 bacteriophage-resistant mutants of Streptococcus thermophilus CHCC23369

| | Viscosity - TADM pressure (mPa) |
|---|---|
| Commercial texturizing strain | -496.2 |
| Mutant CHCC27510 | -934.8 |
| Mutant CHCC27512 | -969.6 |
| Mutant CHCC27806 | -938.0 |
| Commercial starter | -1297.6 |
| Starter with CHCC27510 | -1297.4 |
| Starter with CHCC27512 | -1390.5 |
| Starter with CHCC27806 | -1520.0 |

As will appear from Table 5, all of the mutants had an increased viscosity as compared to the commercial texturizing strain, both when grown as single strains and as a starter culture blend.

Example 5: Acidification Time and Texturizing Capacity (Shear Stress) of 3 Bacteriophage-Resistant Mutants of Streptococcus Thermophilus CHCC23369

The Streptococcus thermophilus (St) mutants CHCC27510, CHCC27511 and CHCC27512 and the mother strain CHCC23369 were tested in a process for producing yogurt for their acidification time and texturizing capacity (shear stress). The mutants were tested both as single culture and in combination with a conventional Lactobacillus delbrueckii subsp. bulgaricus strain used in commercial yogurt starter cultures.

Materials

B-milk: Re-constituted milk with a dry matter content of 9.5 %, which had been heat treated to 99° C. for 30 minutes in a batch process.
Spectrometer (GeneQuant™ 1300, GE Healthcare) for measuring OD
CINAC (AMS, France) for pH logging
Anton Paar Physica Rheometer with ASC, Automatic Sample Changer
Stick fitted with a perforated disc.

Shear Stress

The shear stress was measured using the method specified in Example 3.

Growth of Cultures 10 sample tubes containing M17 broth with 2 % lactose was incubated overnight (>16 Hours) at 37° C. The OD of the overnight cultures was measured and the samples were diluted so as to have the same OD. A 1% solution of the *Lactobacillus delbrueckii* subsp. *bulgaricus* (Lb) strain was prepared.

Cold B-milk was inoculated with 2 % St mutant or mother strain for single cultures and with 2 % St mutant or mother strain and Lb for the St + Lb blends. The Lb represents approx. 10 % of the St + Lb blend. The sample bottles were immersed in a cold water bath with a calibrated CINAC electrode attached. The water bath was programmed to remain cold for 6-8 hours before heating to 43° C. The fermentation takes place at 43° C. until the pH reaches 4.55 for single strains and 4.2 for St + Lb blends. When the target pH was reached, the samples were stirred 20 times gently with the stick with the perforated disc to homogeneity and then cooled to 5° C.

The day after fermentation, the samples were stirred gently again until homogeneity. 20 ml of the samples were introduced to a measuring cup of the Rheometer and brought to 13° C. The rheological properties of the sample were assessed on the Rheometer.

Results

Acidification Time and Shear Stress

TABLE 6

Acidification time of *Streptococcus thermophilus* CHCC23369 and 3 mutants thereof as single culture and in a blend with a *Lactobacillus delbrueckii* subsp. *bulgaricus* (Lb)

| | Acidification time (time to pH 4.55 or 4.2 (min)) | Acidification time as compared to mother strain (%) | Shear stress (Pa) | Shear stress as compared to mother strain (%) |
|---|---|---|---|---|
| Mother strain CHCC23369 | 512 | 100.0 | 45.6 | 100.0 |
| Mutant CHCC27510 | 480 | 93.8 | 45.2 | 99.1 |
| Mutant CHCC27511 | 488 | 95.3 | 46.0 | 100.8 |
| Mutant CHCC27512 | 504 | 98.4 | 45.0 | 98.7 |
| Mother strain CHCC23369 + Lb | 356 | 100.0 | 68.5 | 100.0 |
| CHCC27510 + Lb | 352 | 98.9 | 69.4 | 101.3 |
| CHCC27511 + Lb | ND | ND | 69.4 | 101.3 |
| CHCC27512 + Lb | 352 | 98.9 | 68.9 | 100.6 |

As will appear from Table 6, all of the mutants had a reduced acidification time as compared to the mother strain, both when grown as single strains and as a ST + Lb blend.

As will also appear from Table 6, one of the mutants had an increased shear stress as compared to the mother strain, when grown as single strains. Furthermore, all of the mutants had an increased shear stress as compared to the mother strain, when grown as a St + Lb blend.

Example 6: Acidification Time and Texturizing Capacity (shear Stress) of 1 Bacteriophage-Resistant Mutant of *Streptococcus Thermophilus* CHCC23369

The *Streptococcus thermophilus* (St) mutant CHCC27806 was tested in a process for producing yogurt for its acidification time and texturizing capacity (shear stress). The mutant was tested as a texturizing strain in 3 full yogurt starter cultures comprising a total of 3 or 4 *Streptococcus thermophilus* (st) strains and one *Lactobacillus delbrueckii* subsp. *bulgaricus* (Lb) strain and one probiotic strain (BB12). A starter culture containing CHCC27806 as main texturizing *Streptococcus thermophilus* strain was compared to the corresponding starter cultures, wherein the CHCC27806 strain was replaced by a widely used commercial texturizing *Streptococcus thermophilus* strain (reference starter cultures).

Milk Base

TABLE 7

| Milk base | | | | |
|---|---|---|---|---|
| | Amount | Protein | Carbohydrate | Fat |
| Water | 805 g | | | |
| Skimmed milk powder (SMP) | 15 g | | | |
| Whole milk powder (WMP) | 130 g | | | |
| Sucrose | 50 g | | | |
| Milk base | 1000 g | 3.60 % | 10.88 % | 3.46 % |

Composition of Cultures Tested

The cultures are prepared from frozen DVS (Direct Vat System) cultures.

TABLE 8

| Composition of cultures tested | | | |
|---|---|---|---|
| | Texturizing St | Commercial Lb | Other St and BB12 |
| CHCC27806 culture 1 | CHC-C27806 | Lb1 | 2 commercial St and BB12 |
| Reference culture 1 | St1 | Lb1 | 2 commercial St and BB12 |
| CHCC27806 culture 2 | CHC-C27806 | Lb2 | 3 commercial St and BB12 |
| Reference culture 2 | St1 | Lb2 | 3 commercial St and BB12 |
| CHCC27806 culture 3 | CHC-C27806 | Lb3 | 3 commercial St and BB12 |
| Reference culture 3 | St2 | Lb3 | 3 commercial St and BB12 |

St1 and St2 are commercial texturizing *Streptococcus thermophilus* strains.
Lb1, Lb2 and Lb3 are commercial *Lactobacillus delbrueckii* subsp. *bulgaricus* strains Materials CINAC (AMS, France) for pH logging
Anton Paar Physica Rheometer with ASC, Automatic Sample Changer
Stick fitted with a perforated disc.

Shear Stress

The shear stress was measured using the method specified in Example 3.

Growth of Cultures

Baby bottles (200 ml) were filed with 195 ml milk base and inoculated with the cultures. The bottles were transferred to a water bath with a temperature of 43° C. and incubated at this temperature in a CINAC apparatus until a pH of 4.30 is reached. The pH during acidification of the samples was measured in the CINAC apparatus for a minimum of 20 hours or 4 hours after a pH of 4.30 was reached.

Results

Acidification Time and Shear Stress

TABLE 9

Acidification time and shear stress of a yogurt starter culture containing commercial strains, wherein a texturizing Streptococcus thermophilus strain has been replaced by CHCC27806.

|  | Time to pH 4.30 (Hours) | Shear stress (Pa) |
| --- | --- | --- |
| CHCC27806 culture 1 | 9.13 | 72.1 |
| Reference culture 1 | 10.07 | 66.7 |
| CHCC27806 culture 2 | 8.62 | 54.6 |
| Reference culture 2 | 8.88 | 49.3 |
| CHCC27806 culture 3 | 9.24 | 48.7 |
| Reference culture 3 | 9.32 | 47.5 |

As will appear from Table 9, the starter cultures containing the CHCC27806 strain of the invention had a lower acidification time and a higher texture as measured by shear stress as compared to the corresponding culture containing a reference commercial texturizing *Streptococcus thermophilus* strain.

Example 7: Acidification Time and Texturizing Capacity (Shear Stress) of 1 Bacteriophage-Resistant Mutant of *Streptococcus Thermophilus* CHCC23369 in Two Commercial Yogurt Starter Cultures The *Streptococcus thermophilus* (St) mutant CHCC27806 was tested in a process for producing yogurt for its acidification time and texturizing capacity (shear stress). The mutant was tested as a texturizing strain in two commercial yogurt starter cultures, Yoflex Premium 1.0 and Nutrish BMY-03. The two commercial cultures (reference) were compared to the corresponding cultures, wherein the texturizing strain of the commercial cultures had been replaced by CHCC27806.

Milk Base

The milk base has a fat content of 1 % and a protein content of 4.5 %.

Shear Stress

The shear stress was measured using the method specified in Example 3.

Growth Of Cultures

The experiment was conducted in the same way as in Example 6 with the exception that the target pH was 4.55.

Results

Acidification Time and Shear Stress

TABLE 10

Acidification time and shear stress of two commercial cultures, wherein a texturizing Streptococcus thermophilus strain has been replaced by CHCC27806.

|  | Time to pH 4.55 (minutes) | Shear stress (Pa) |
| --- | --- | --- |
| Yoflex Premium 1.0 (reference) | 560 | 73.40 |
| Yoflex Premium 1.0 with CHCC27806 | 552 | 73.70 |
| Nutrish BMY-03 (reference) | 520 | 73.40 |
| Nutrish BMY-03 with CHCC27806 | 512 | 74.90 |

As will appear from Table 10, the two starter cultures containing the CHCC27806 strain of the invention had a lower acidification time and a higher texture as measured by shear stress as compared to the corresponding commercial reference cultures.

Example 8: Acidification Time and Texturizing Capacity (Shear Stress) of 1 Bacteriophage-Resistant mutant of *Streptococcus Thermophilus* CHCC23369 in a Commercial Yogurt Starter Culture The *Streptococcus thermophilus* (St) mutant CHCC27806 was tested in a process for producing yogurt for its acidification time and texturizing capacity (shear stress). The mutant was tested as a texturizing strain in a commercial yogurt starter culture, Yoflex Mild 1.0. The commercial culture (reference) was compared to the corresponding culture, wherein the texturizing strain of the commercial culture had been replaced by CHCC27806.

Shear Stress

The shear stress was measured using the method specified in Example 3.

Milk Base

TABLE 11

| | Milk base | | | |
| --- | --- | --- | --- | --- |
| | Amount | Protein | Carbohydrate | Fat |
| Skimmed milk | 14478 g | | | |
| 1.5 % fat milk | 26060 g | | | |
| Skimmed milk powder (SMP) | 1462 g | | | |
| Milk base | 42000 g | 4.5 % | 6.45 % | 1.0 % |

Growth of Cultures

The fermentation was carried out in 5000 ml fermentor tanks at a temperature of 43° C. Fermentation was continued until an end pH of 4.55 was reached. pH was measured continuously during the fermentation.

Results

Acidification Time and Shear Stress

TABLE 12

Acidification time and shear stress of a commercial culture, wherein a texturizing *Streptococcus thermophilus* strain has been replaced by CHCC27806.

| | Time to pH 4.55 (hour and minutes) | Shear stress (Pa) |
|---|---|---|
| Yoflex Mild 1.0 (reference) | 7 h 0 m | 58.45 |
| Yoflex Mild 1.0 with CHCC27806 | 6 h 25 m | 60.75 |

As will appear from Table 12, the starter culture containing the CHCC27806 strain of the invention had a lower acidification time and a higher texture as measured by shear stress as compared to the corresponding commercial reference culture.

DEPOSITS AND EXPERT SOLUTION

The Applicant requests that a sample of the deposited microorganism should be made available only to an expert approved by the Applicant.

The strains of the invention have been deposited previously and have the following accession numbers:

*Streptococcus thermophilus* strain CHCC23369 deposited as DSM32502 on 2017-05-09 at Deutsche Sammlung von Mikroorganismen und Zellkulturen GmbH (DSM), Inhoffenstr. 7B, D-38124 Braunschweig.

*Streptococcus thermophilus* strain CHCC27806 deposited as DSM32503 on 2017-05-09 at Deutsche Sammlung von Mikroorganismen und Zellkulturen GmbH (DSM), Inhoffenstr. 7B, D-38124 Braunschweig.

*Streptococcus thermophilus* strain CHCC27510 deposited as DSM32504 on 2017-05-09 at Deutsche Sammlung von Mikroorganismen und Zellkulturen GmbH (DSM), Inhoffenstr. 7B, D-38124 Braunschweig.

*Streptococcus thermophilus* strain CHCC27511 deposited as DSM32505 on 2017-05-09 at Deutsche Sammlung von Mikroorganismen und Zellkulturen GmbH (DSM), Inhoffenstr. 7B, D-38124 Braunschweig.

*Streptococcus thermophilus* strain CHCC27512 deposited as DSM32506 on 2017-05-09 at Deutsche Sammlung von Mikroorganismen und Zellkulturen GmbH (DSM), Inhoffenstr. 7B, D-38124 Braunschweig.

*Streptococcus thermophilus* strain CHCC27513 deposited as DSM32507 on 2017-05-09 at Deutsche Sammlung von Mikroorganismen und Zellkulturen GmbH (DSM), Inhoffenstr. 7B, D-38124 Braunschweig.

Bacteriophage CHPC1008 deposited as DSM32517 on 2017-05-09 at Deutsche Sammlung von Mikroorganismen und Zellkulturen GmbH (DSM), Inhoffenstr. 7B, D-38124 Braunschweig.

Bacteriophage CHPC1057 deposited as DSM23962 on 2010-08-27 at Deutsche Sammlung von Mikroorganismen und Zellkulturen GmbH (DSM), Inhoffenstr. 7B, D-38124 Braunschweig.

The deposits were made according to the Budapest Treaty on the international recognition of the deposit of microorganisms for the purposes of patent procedure.

The Applicant requests that a sample of the deposited microorganism should be made available only to an expert approved by the Applicant.

The invention claimed is:

1. A method of producing a *Streptococcus thermophilus* strain, comprising:
    (a) providing *Streptococcus thermophilus* strain CHCC23369 deposited at Deutsche Sammlung von Mikroorganismen und Zellkulturen GmbH (DSMZ) under Accession Number DSM32502 as a mother strain,
    (b) growing a culture of the mother strain in the presence of a bacteriophage to which the mother strain is not resistant, to obtain a number of mutant strains resistant to the bacteriophage,
    (c) measuring an acidification time of the bacteriophage-resistant mutant strains and the mother strain in a milk base and selecting a mutant strain with a reduced acidification time as compared to the mother strain, to obtain a fast-acidifying *Streptococcus thermophilus* mutant strain.

2. A method according to claim 1, wherein the bacteriophage is one or more selected from the group consisting of CHPC1008 deposited at DSMZ under Accession Number DSM32517, and CHPC1057 deposited at DSMZ under Accession Number DSM23962.

3. A method according to claim 1, wherein in step (c) the selected mutant strain has an acidification time of less than 99% of the acidification time of the mother strain.

4. A method according to claim 1, wherein in step (c) the bacteriophage-resistant mutant strains and the mother strain are grown as single cultures.

5. A method according to claim 1, wherein in step (c) the bacteriophage-resistant mutant strains and the mother strain are grown as a mixed culture which further comprises at least one *Lactobacillus delbrueckii* spp. *bulgaricus* strain.

6. A method according to claim 1, further comprising:
    (d) measuring a texturizing capacity of the mutant strains selected in step (c) and the mother strain in a milk base, wherein texturizing capacity of each strain is assessed by fermenting a milk base with the respective strain to obtain a fermented milk product, and assessing shear stress of the fermented milk product at a temperature of 13° C. and shear rate of 300 s-1, and selecting a mutant strain which has a texturizing capacity of least 90% of the texturizing capacity of the mother strain, to obtain a fast-acidifying, texturizing *Streptococcus thermophilus* mutant strain.

7. A method according to claim 6, wherein in step (d) the selected mutant strain has a texturizing capacity of least 95% of the texturizing capacity of the mother strain.

8. A mutant *Streptococcus thermophilus* strain obtained by the method of claim 1.

9. A method of producing a fermented milk product, comprising fermenting a starter culture comprising the mutant strain of claim 8.

10. A fermented milk product containing the mutant strain of claim 8.

* * * * *